(12) United States Patent
Deal (10) Patent No.: US 8,057,461 B2
(45) Date of Patent: *Nov. 15, 2011

(54) SELF-RETAINING STENT

(75) Inventor: Travis Deal, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 697 days.

This patent is subject to a terminal disclaimer.

(21) Appl. No.: 12/060,924

(22) Filed: Apr. 2, 2008

(65) Prior Publication Data

US 2008/0249636 A1    Oct. 9, 2008

Related U.S. Application Data

(63) Continuation of application No. 10/397,502, filed on Mar. 26, 2003, now Pat. No. 7,357,818.

(51) Int. Cl.
*A61M 27/00* (2006.01)
*A61F 2/04* (2006.01)

(52) U.S. Cl. .................................. 604/544; 623/23.7

(58) Field of Classification Search .... 623/23.64–23.66, 623/23.7, 23.69; 606/127, 198–200, 108; 604/544, 541
See application file for complete search history.

(56) References Cited

U.S. PATENT DOCUMENTS

| | | | |
|---|---|---|---|
| 3,108,593 A | 10/1963 | Glassman | |
| 4,973,301 A | 11/1990 | Nissenkorn | |
| 5,052,998 A | 10/1991 | Zimmon | |
| 5,322,501 A | 6/1994 | Mahmud-Durrani | |
| 5,518,498 A | 5/1996 | Lindenberg et al. | |
| 5,599,291 A | 2/1997 | Balbierz et al. | |
| RE35,849 E | 7/1998 | Soehendra | |
| 5,795,319 A | 8/1998 | Ali | |
| 5,827,276 A | 10/1998 | Le Veen et al. | |
| 5,885,258 A | 3/1999 | Sachdeva et al. | |
| 5,907,893 A | 6/1999 | Zadno-Azizi et al. | |
| 5,964,744 A | 10/1999 | Balbierz et al. | |
| 6,007,558 A | 12/1999 | Ravenscroft et al. | |
| 6,074,416 A | 6/2000 | Berg et al. | |
| 6,364,868 B1 | 4/2002 | Ikeguchi | |
| 6,767,339 B2 | 7/2004 | Reydel | |

(Continued)

FOREIGN PATENT DOCUMENTS

WO    WO 97/17094    5/1997

(Continued)

OTHER PUBLICATIONS

International Search Report for PCT Application No. US2004/009022 filed Mar. 25, 2004, 4 pages.

*Primary Examiner* — Thomas J Sweet
*Assistant Examiner* — Cheryl Miller
(74) *Attorney, Agent, or Firm* — Brake Hughes Bellermann LLP (57) ABSTRACT

A stent is designed to be placed in a lumen of a patient and extend therethrough. The stent includes a distal end and a proximal end. The distal end includes a distal retention structure and the proximal end includes a plurality of radially extending flexible segments to prevent migration of the stent through the lumen. At least one radially extending flexible segment at the proximal end is able to assume an outwardly everted configuration. The stent of the invention, due to its dimensions, shape, and rigidity, minimizes the force of contact and abrasion to sensitive areas of the patient's body, such as the trigone region of the bladder and the ureteral-vesical junction.

14 Claims, 8 Drawing Sheets

U.S. PATENT DOCUMENTS

| | | | |
|---|---|---|---|
| 6,849,069 B1 | 2/2005 | Clayman et al. | |
| 6,908,447 B2 | 6/2005 | McWeeney et al. | |
| 6,926,690 B2 | 8/2005 | Renati | |
| 6,929,621 B2 | 8/2005 | Whitmore et al. | |
| 6,994,717 B2 * | 2/2006 | Konya et al. | 606/200 |
| 7,357,818 B2 * | 4/2008 | Deal | 623/23.66 |
| 2001/0047164 A1 | 11/2001 | Teague et al. | |
| 2001/0049494 A1 | 12/2001 | Liu | |
| 2001/0053936 A1 | 12/2001 | Whitmore, III | |
| 2002/0007222 A1 | 1/2002 | Desai | |
| 2002/0032487 A1 | 3/2002 | Dua et al. | |
| 2002/0183852 A1 | 12/2002 | McWeeney | |
| 2003/0078671 A1 | 4/2003 | Lesniak et al. | |
| 2003/0109930 A1 | 6/2003 | Bluni et al. | |
| 2005/0131547 A1 | 6/2005 | Segura et al. | |
| 2005/0240279 A1 | 10/2005 | Kagan et al. | |

FOREIGN PATENT DOCUMENTS

| | | |
|---|---|---|
| WO | WO 00/51521 | 9/2000 |
| WO | WO 00/74582 | 12/2000 |
| WO | WO 03/049796 | 6/2003 |

* cited by examiner

US 8,057,461 B2

SELF-RETAINING STENT

CROSS-REFERENCE TO RELATED APPLICATIONS

This application claims priority to and is a continuation of U.S. patent application Ser. No. 10/397,502, entitled "Self-Retaining Stent," filed Mar. 26, 2003, now U.S. Pat. No. 7,357,818, which is incorporated herein by reference in its entirety.

TECHNICAL FIELD

The invention generally relates to medical devices for drainage of fluids, and more specifically to stents.

BACKGROUND INFORMATION

A ureter is a tubular passageway in a body that carries urine from a kidney to a bladder. Ureteral stents are used to assist urinary drainage from the kidney to the urinary bladder in patients with a ureteral obstruction or injury, or to protect the integrity of the ureter during a variety of surgical manipulations. Stents may be used to treat or avoid ureteral obstructions (such as ureteral stones or ureteral tumors), which disrupt the flow of urine from the kidneys to the bladder. Serious obstructions may cause urine to back up into the kidneys, threatening renal function. Ureteral stents may also be used after endoscopic inspection of the ureter to prevent obstruction of the ureter by swelling of the ureteral wall caused by the surgical procedure.

Ureteral stents typically are tubular in shape and terminate in two opposing ends: a kidney-end and a bladder-end. One or both of the ends may be shaped in a way to prevent the upward downward migration of the stent due, for example, to physiological movements. The ends may be coiled in a pigtail or J-shape to retain their position in the ureter. A kidney-end coil resides within a lumen of the kidney, known as the renal pelvis, and is designed to prevent stent migration down the ureter and into the bladder. Similarly, the bladder-end coil resides in the bladder and is designed to prevent stent migration upward toward the kidney. The bladder coil may also be used to aid in retrieval and removal of the stent.

Regions such as the trigone region in the bladder and the region of the ureter near the bladder known as the ureteral-vesical junction are particularly sensitive and thus prone to irritation by foreign objects. Commonly used bladder-end coils contact and irritate these regions causing discomfort to the patient. Moreover, ureteral stents particularly the bladder-end, may produce adverse effects including blood in the urine, a continual urge to urinate, and strangury. Thus, while providing drainage from the kidney to the bladder, stents may also cause or contribute to significant patient discomfort and serious medical problems.

SUMMARY OF THE INVENTION

The invention generally relates to medical devices to provide drainage, more particularly to stents, and more particularly to ureteral stents that reduce patient discomfort by minimizing contact between the stent and regions of the body of the patient, including the trigone region and the ureteral-vesical junction. In particular, the invention relates to a stent with a bladder-end that includes a plurality of radially extending flexible segments, which form the bladder retention structure. The bladder retention structure of the stent reduces patient discomfort by minimizing the contact and abrasion between the retention structure and the trigone region and the ureteral-vesical junction of the patient. The retention structure is generally located within the urinary bladder when the stent is placed within the ureter of a patient. The plurality of radially extending flexible segments at the bladder-end function to maintain a proximal end of the stent within the bladder and thus prevent the stent from migrating towards the kidney.

It is noted initially that the directional terms proximal and distal require a point of reference. As used herein, the point of reference is from the perspective of a medical professional. Therefore, the term distal refers to a direction that points into the body of the patient and away from the medical professional, whereas the term proximal refers to a direction that points out of the patient's body.

The shape and composition of the bladder-end or proximal retention structure reduces patient discomfort. The proximal retention structure is formed in a shape that minimizes contact between the radially extending flexible segments of the proximal retention structure and the trigone region of the bladder, thus reducing patient discomfort. The radially extending flexible segments are also sufficiently thin and flexible to minimize the force of contact and abrasion to the sensitive regions of the urinary tract including the trigone region. The plurality of radially extending flexible segments that form the proximal retention structure are, however, sufficiently resilient such that the shape of the proximal retention structure is generally maintained while the stent is in the body.

In one aspect, the invention is directed to a ureteral stent for facilitating drainage from a kidney to a bladder of a patient including an elongated member that includes a proximal end, a distal end, and a length sufficient to extend substantially along an entire length of a ureter of a patient. The elongated member defines a lumen extending at least partially therethrough. The stent further includes a plurality of radially extending flexible segments extending from the proximal end. At least one of the segments is able to assume an outwardly everted configuration to inhibit movement of the segments from the bladder into the ureter after the stent is placed within the patient. A kidney portion extends from the distal end of the stent for receiving urine after placement of the stent within the patient and for passing at least some of the received urine into the lumen of the elongated member. The kidney portion is able to assume a configuration to inhibit movement of the kidney portion into the ureter once inserted into the patient.

In some embodiments of the foregoing aspect of the invention, an outside dimension of the assumed configuration of the kidney portion is larger than an outside diameter of the elongated member at the distal end. In another embodiment, the kidney portion can include a coiled shape. In yet another embodiment, the coiled shape can be conical, spherical, helical, frusto-conical, or combinations thereof.

In another aspect, the invention relates to a stent including an elongated member including a proximal end and a distal end and defining a lumen extending at least partially through the elongated member. The stent further includes a plurality of radially extending flexible segments disposed adjacent to the proximal end. At least one of the radially extending flexible segments is able to assume an outwardly everted configuration to inhibit movement of the segments into a lumen of a patient after the stent is placed within the patient. A distal retention structure is disposed adjacent to the distal end to inhibit movement of the distal end into the lumen of the patient after inserting the stent within the patient.

In some embodiments of the foregoing aspect of the invention, an outside dimension of the distal retention structure is larger than the an outside diameter of the elongated member in the distal end. In a further embodiment, the distal retention structure can include a coiled shape. In another embodiment, the coiled shape can be conical, spherical, helical, frusto-conical, or combinations of the foregoing. In yet another embodiment, the elongated member can have a length sufficient to extend substantially along an entire length of a ureter of the patient.

In various embodiments of the foregoing aspects of the invention, an outside diameter of the plurality of radially extending flexible segments is larger than an outside diameter of the proximal end of the elongated member. In other embodiments, the outside diameter of the segments can be between about 3 cm to about 5 cm. In yet other embodiments, the plurality of radially extending flexible segments can be resilient. In further embodiments of the foregoing aspects of the invention, at least six radially extending flexible segments can extend from the proximal end.

In yet another aspect, the invention relates to a method of placing a stent in the body of a patient. The method includes the steps of providing a stent, inserting the stent into a lumen of the patient, and positioning the stent in the patient such that a plurality of radially extending flexible segments and a distal retention structure inhibit migration of the stent in the lumen of the patient. The stent includes an elongated member including a proximal end and a distal end and defining a lumen extending at least partially through the elongated member. The plurality of radially extending flexible segments extends from the proximal end in one embodiment. At least one of the radially extending flexible segments is able to assume an outwardly everted configuration to inhibit movement of the segments into the lumen of the patient after placement of the stent within the patient. The distal retention structure extends from the distal end to inhibit movement of the distal end through the lumen of the patient after placing the stent within the patient.

In some embodiments, the method includes the step of disposing a stylet within the lumen of the elongated member to maintain the distal retention structure in a substantially linear configuration prior to inserting the stent. In other embodiments, the method includes the step of disposing the stent within a flexible sheath to maintain the radially extending flexible segments in a substantially linear configuration prior to inserting the stent. In one embodiment, the method includes the step of removing the flexible sheath after positioning the stent within the patient, thereby deploying the radially extending flexible segments. In another embodiment, the method includes the step of removing the stylet after positioning the stent within the patient, thereby deploying the distal retention structure.

In various embodiments of the foregoing aspect of the invention, an outside diameter of the plurality of radially extending flexible segments is larger than an outside diameter of the elongated member at the proximal end, and an outside dimension of the distal retention structure may be larger than an outside diameter of the elongated member at the distal end. Further, the stent can be placed within a ureter of the patient and the plurality of radially extending flexible segments can be disposed within a bladder and the distal retention structure is disposed within a kidney.

In still another aspect, the invention relates to a method of making a stent for maintaining the flow of a bodily fluid in a patient. The method includes the steps of providing an elongated member and sectioning a proximal portion of the elongated member into a plurality of segments oriented substantially parallel to a longitudinal axis of the elongated member. The method also includes the step of shaping at least one of the segments to assume a radial, outwardly everted configuration to inhibit movement of the segments into a lumen of a patient after placement of the stent within the patient. The elongated member includes a lumen.

In one embodiment of the foregoing aspect of the invention, the providing step includes forming the elongated member by injection molding. In another embodiment, the providing step includes forming the elongated member by extrusion. In yet another embodiment, the sectioning step includes securing the elongated member in an indexing fixture and cutting the proximal portion with a blade. In some embodiments of the invention, the shaping step includes bending at least one of the segments around a form mold and fixing the at least one segment in the radial, outwardly everted configuration. The fixing step may include thermosetting the at least one segment at about 140-160° C.

The foregoing and other objects, aspects, features, and advantages of the invention will become more apparent from the following description and from the claims.

BRIEF DESCRIPTION OF THE DRAWINGS

In the drawings, like reference characters generally refer to the same pars throughout the different views. Also, the drawings are not necessarily to scale, emphasis generally being placed upon illustrating the principles of the invention. In the following description, various embodiments of the present invention are described with reference to the following drawings, in which.

DESCRIPTION

Embodiments of the present invention are described below. It is, however expressly noted that a stent in accordance with the present invention is not limited to use as a ureteral stent, but rather the stent may be used in essentially any lumen within a body.

One embodiment of the invention generally relates to a ureteral stent that minimizes discomfort when positioned within a lumen of a patient. The stent of the present invention includes a proximal retention structure that includes a plurality of radially extending flexible segments, wherein at least one segment is able to assume an outwardly everted configuration. Due to its dimensions, shape, and flexibility, the proximal retention structure minimizes the force of contact and abrasion to sensitive areas outside one end of the lumen. When the stent is used as a ureteral stent, the proximal retention structure minimizes irritation to the trigone region of the bladder and the ureteral-vesical junction.

Figure 1:
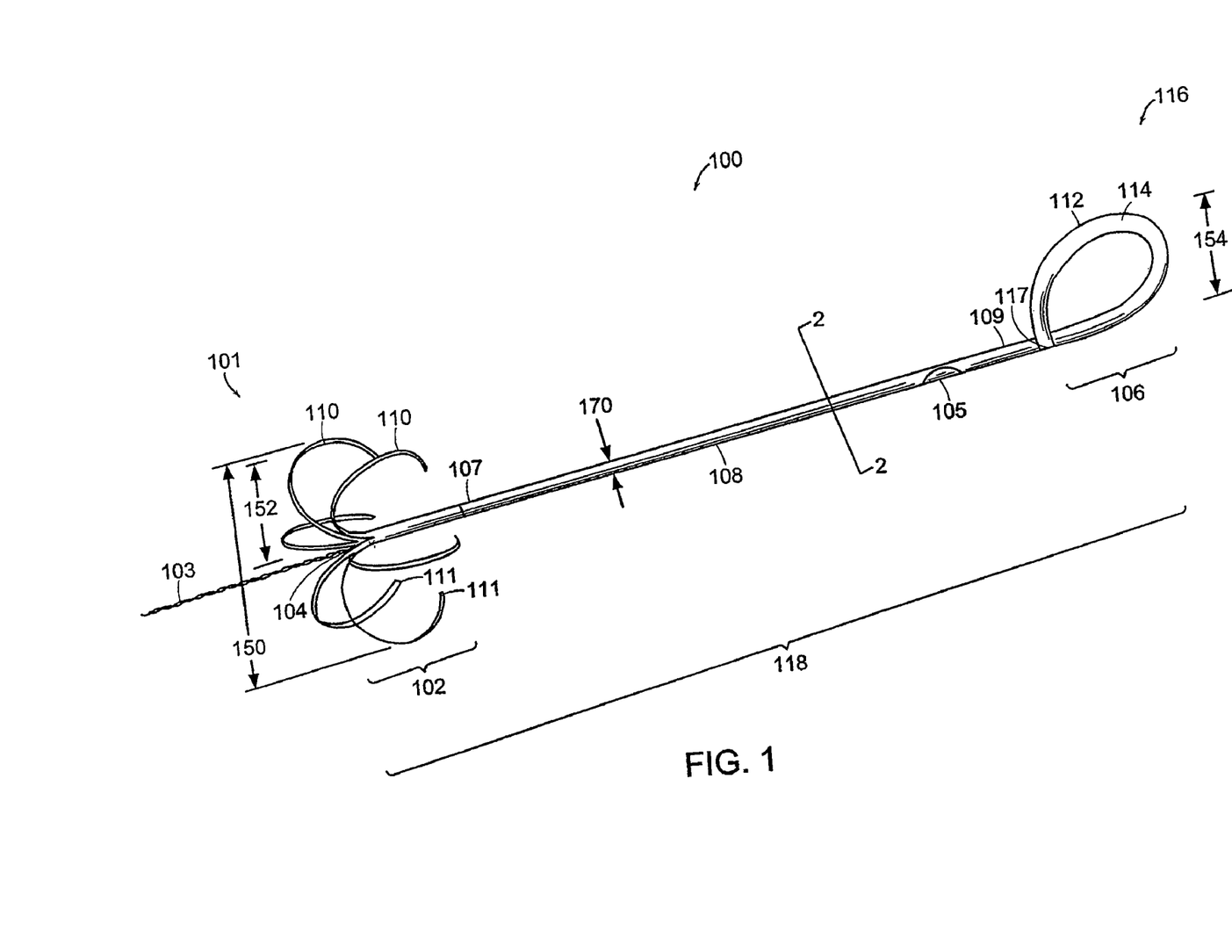
FIG. 1 depicts an embodiment of a stent in accordance with the invention.

Referring to FIG. 1, a ureteral stent 100 includes an elongated member 118 that includes a proximal portion 102, a distal portion 106, and a central body 108. The proximal portion 102 includes a plurality of radially extending flexible segments 110 (six are depicted) that form a proximal retention structure 101. The radially extending flexible segments 110 extend from a proximal end 107 of the central body 108 in an outwardly everted configuration. The distal portion 106 of the stent 100 also includes a distal or kidney retention structure 116 extending from a distal end 109 of the central body 108. The stent 100 further includes the central body 108 interposed between the proximal end 107 and the distal end 109. A lumen 105 passes at least partially through the length of the elongated member 118 and is defined by the elongated member 118. In one embodiment, the elongated member 118 has an opening 104 at the proximal portion 102 and at least one opening 114 in the distal portion 106. Openings 104 and 114 are in fluid communication with the lumen 105. One or more openings may be provided along the length of the central body in fluid communication with the lumen 105.

Figure 2A:
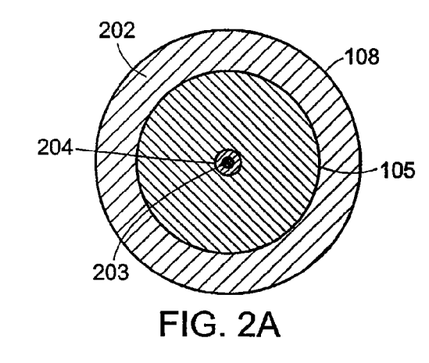
FIG. 2A is a schematic transverse cross-sectional view of the stent of FIG. 1 taken at line 2-2.
Figure 2B:
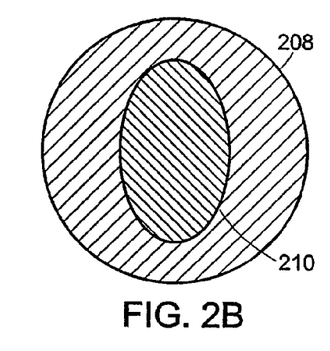
FIGS. 2B-2D are schematic transverse cross-sectional views of alternative embodiments of a stent in accordance with the invention.
Figure 2C:
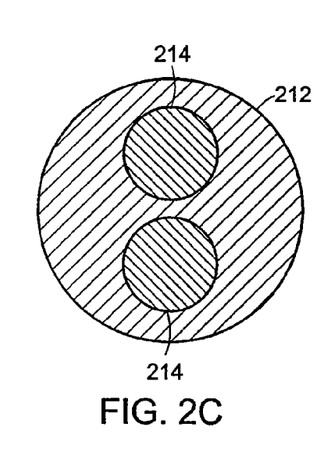
Figure 2D:
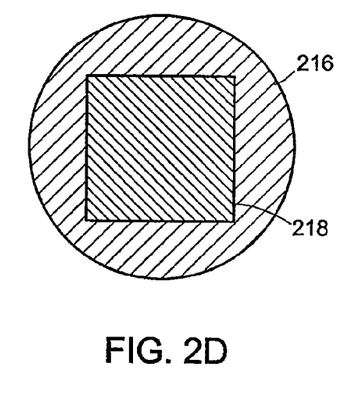

FIG. 2A is a cross-section of the stent 100 of FIG. 1 illustrating the lumen 105 that exists in at least a portion of the elongated member 118. FIGS. 2B-2D depict alternative cross-sectional views of the elongated member 118. In one embodiment of the invention, shown in FIG. 2A, a circular lumen 105 is defined by the central body 108. FIG. 2B depicts an alternative embodiment of a stent with an elliptical lumen 210 defined by a central body 208. FIG. 2C depicts yet another alternative embodiment, wherein a central body 212 defines multiple circular lumens 214. In some embodiments, the cross-sectional configurations of the multiple lumens 214 can be circular, elliptical, polygonal wedge-shaped or any combination thereof. In yet another alternative embodiment, as shown in FIG. 2D, a square lumen 218 is defined by the central body 216.

The various configurations may include different numbers of lumens of various sizes. Moreover, a lumen may be shaped specifically to receive or to be compatible with guide wires, cannula, or other devices. The inner diameters or dimensions, the number, and the arrangement of lumen(s) within the stent 100 may be varied to suit a particular application, for example, to alter physical properties of the stent 100 and/or the rate of urine flow therethrough. For example, in FIG. 2A the longitudinal center axis 203 of the lumen 105 is arranged coaxially with the longitudinal center axis 204 of the central body 108. Alternatively, the longitudinal center axes 203 and 204 can be arranged abaxially to one another.

Referring back to FIG. 2A, the wall 202 of the lumen 105 is of sufficient thickness to resist the pressure from adjacent tissue caused by, for example, a tumor, peristalsis, or swelling that would restrict the ureter 405 (See FIG. 4A) if not for the presence of the ureteral stent 100. For example, the wall thickness may range from about $2.5 \times 10^{-3}$ to about $2.0 \times 10^{-3}$ mm. In a particular embodiment, the ureteral stent 100 has a wall thickness of about $2.1 \times 10^{-3}$ μm. In one embodiment, the radially extending flexible segments 110 are produced by sectioning the proximal portion 102 of the elongated member 118 (See FIG. 5B). In that case, the thickness of the segments 110 are determined by the wall thickness of the elongated member 118. Where a greater wall thickness is desired, the high degree of flexibility of the segments 110 may be compromised. In that case, radially extending flexible segments 110 of lesser thickness may be prepared and later attached to the proximal end 107 of the central body 108 (See FIGS. 5C and 5D).

The outside diameter 170 of the central body 108 may range from about 4 French to about 9 French. Depending on the size of the patient, an acceptable range for the outside diameter 170 of the central body 108 is about 4.8 French to about 7.3 French. When a larger diameter is required, such as, for example, when a higher flow or a greater stiffness is desired, a central body 108 having a larger outside diameter 170 may be used. An acceptable larger outside diameter 170 of the central body 108 may be about 8 French to about 12 French. Where larger diameters are employed, it may be desirable to prepare the proximal retention structure 101 separately to ensure that the segments 110 maintain a high degree of flexibility.

The length of the central body 108 may also vary to suit a particular application, for example, the size of the patient and the particular lumen. Referring to FIG. 4B, an acceptable length of the central body 108 positions the proximal end 107 of the central body 108 at the ureteral-vesical junction 408 and the distal end 109 of the central body 108 adjacent to the renal pelvis 403. The length of the central body 108 may range from about 20 cm to about 30 cm, for example.

The radially extending flexible segments 110 are of sufficient length to form a proximal retention structure 101 that is effective in preventing the upward migration of the stent 100, for example, towards the renal pelvis 403. The length of a single segment may range from about 2 cm to about 5 cm. In a particular embodiment, the length of an individual segment 110 is about 4.7 cm. The diameter 152 formed by a single everted segment 110 (See FIG. 1) may range from about 1 cm to about 3 cm and preferably about 2 cm.

To prevent the proximal retention structure 101 from passing through the ureter 405, an outside diameter 150 formed by the radially extending flexible segments 110 should exceed the outside diameter 170 of the proximal end 107 of the central body 108. The outside diameter 150 of the segments 110 may range from about 2 cm to about 6 cm. In a particular embodiment, the outside diameter 150 of the segments 110 is about 4 cm. Detailed methods of producing the radially extending flexible segments 110 are depicted in FIGS. 5A-D.

Figure 3A:
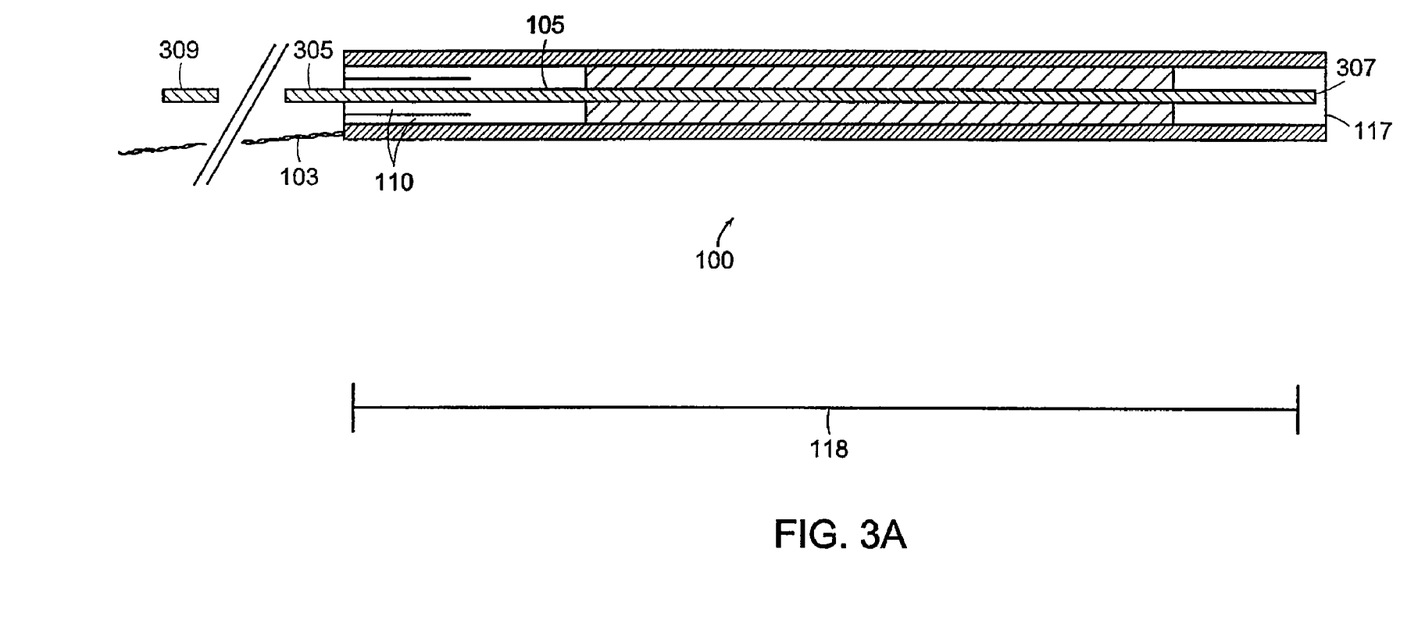
FIG. 3A is a schematic longitudinal cross-sectional view of the stent of FIG. 1 with a stylet disposed therein.
Figure 3B:
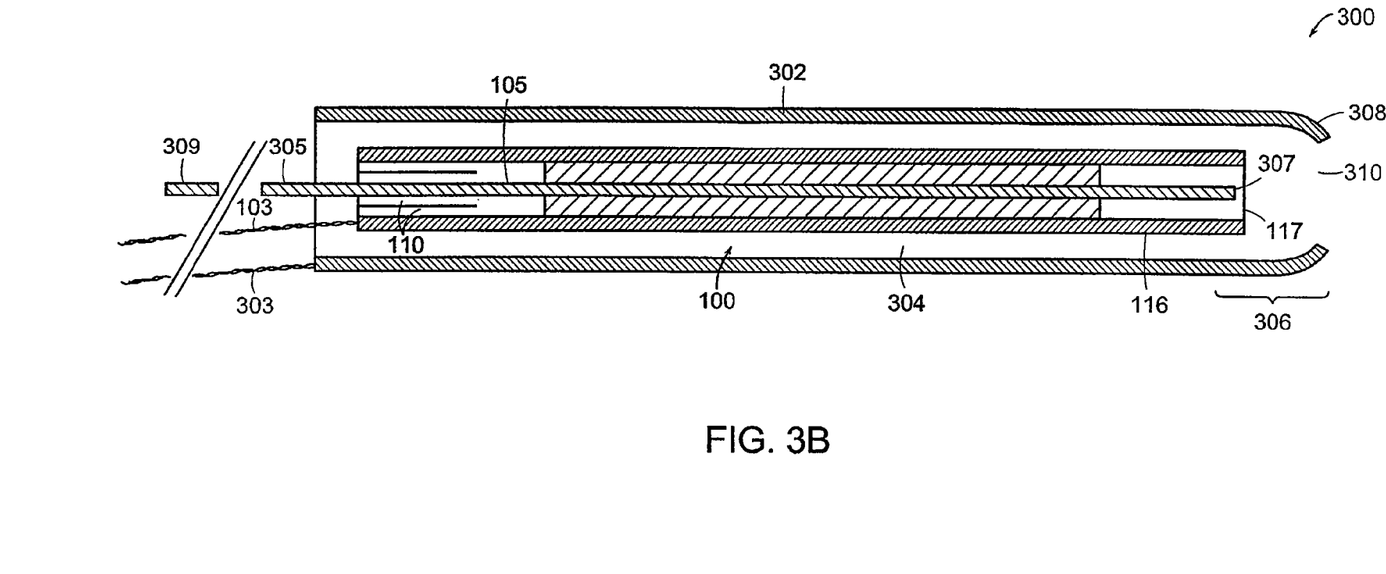
FIG. 3B depicts the ureteral stent of FIG. 3A disposed within a flexible sheath.

In one embodiment of the invention, a medical professional, such as a physician, advances the ureteral stent 100 into the patient's body using a pushing device or stylet 305, as shown in FIGS. 3A and 3B. FIG. 3A depicts a longitudinal cross-section of the ureteral stent 100 showing a stylet 305 disposed within the lumen 105 of the elongated member 118. The radially extending flexible segments 110 are shown in a linear configuration, representing the shape assumed when advancing the stent 100 through the patient's urethra. Due to their high degree of flexibility, the radially extending flexible segments 110 are able to assume a substantially linear configuration upon insertion into the urethral opening 411 of the patient.

The stylet 305 has a distal end 307 and a proximal end 309. The stylet 305 should be long enough such that the distal end 307 of the stylet 305 can contact the distal tip 117 of the elongated member 118, while the proximal end 309 of the stylet 305 remains outside of the patient's body when the ureteral stent 100 is properly positioned within the ureter 405 of the patient (See FIG. 4A). The stylet 305 is sufficiently rigid to deform the distal retention structure 116 into a linear conformation, thus facilitating insertion of the stent 100 into the patient's body.

In an alternative embodiment, a flexible sheath 300 is disposed around the ureteral stent 100 to maintain the elongated member 118 in a linear conformation. FIG. 3B depicts a longitudinal cross-section of the flexible sheath 300 showing the ureteral stent 100 disposed therein. The flexible sheath 300 has a linear cavity 304 defined by an outer wall 302. The leading portion 306 of the flexible sheath 300 includes a tapered tip 308, which facilitates passage through a bodily lumen. A sheath retraction structure 303 is coupled to the outer wall 302 for removing the flexible sheath 300 from the patient after the stent 100 is inserted into the patient. The sheath retraction structure 303 can be a thread-like structure that is disposed in the urethra and extends outside of the patient while a medical professional inserts the stent 100 into the patient's body.

In one embodiment, prior to inserting the ureteral stent 100 into the patient the stent 100 is loaded into the flexible sheath 300. The ureteral stent 100 is oriented in the linear cavity 304 such that the distal retention structure 116 of the elongated member 118 is disposed within the leading portion 306 of the flexible sheath 300. The flexible sheath 300 confines the ureteral stent 100 within the linear cavity 304, causing the elongated member 118 to assume a substantially linear configuration.

To connect the stylet 305 to the ureteral stent 100, the medical professional passes the stylet 305 through the lumen 105 of the elongated member 118 until the distal end 307 of the stylet 305 contacts the distal tip 117 of the elongated member 118. The flexible sheath 300 may then be disposed over elongated member 118 to linearize the radially extending flexible segments 110. The ureteral stent 100, the flexible sheath 300 and the stylet 305 are sufficiently flexible to conform to curvatures encountered in the bodily lumen (See FIG. 4A).

Figure 4A:
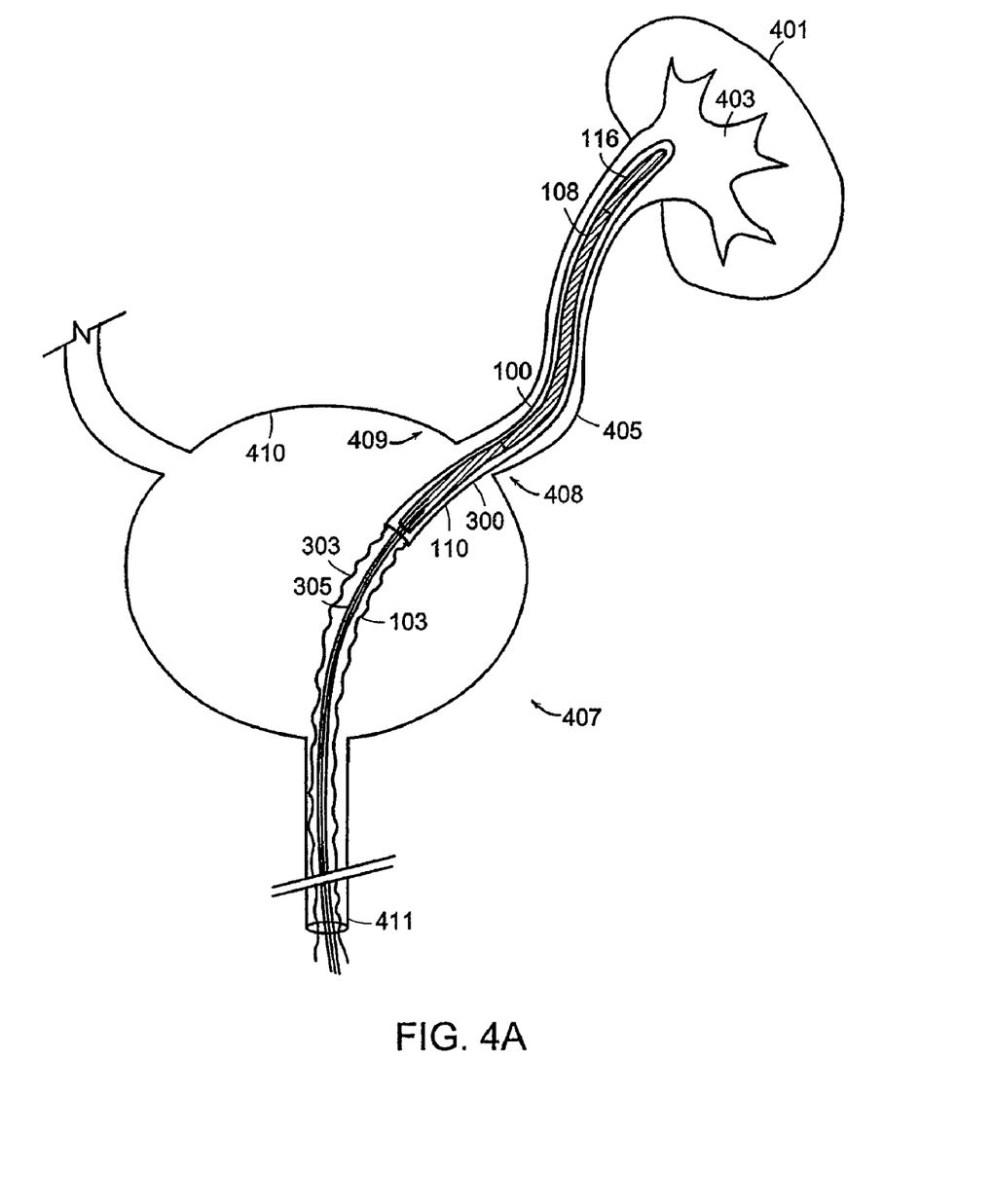
FIGS. 4A and 4B are schematic representations of a method of placing the stent of FIG. 1 in a body of a patient.
Figure 4B:
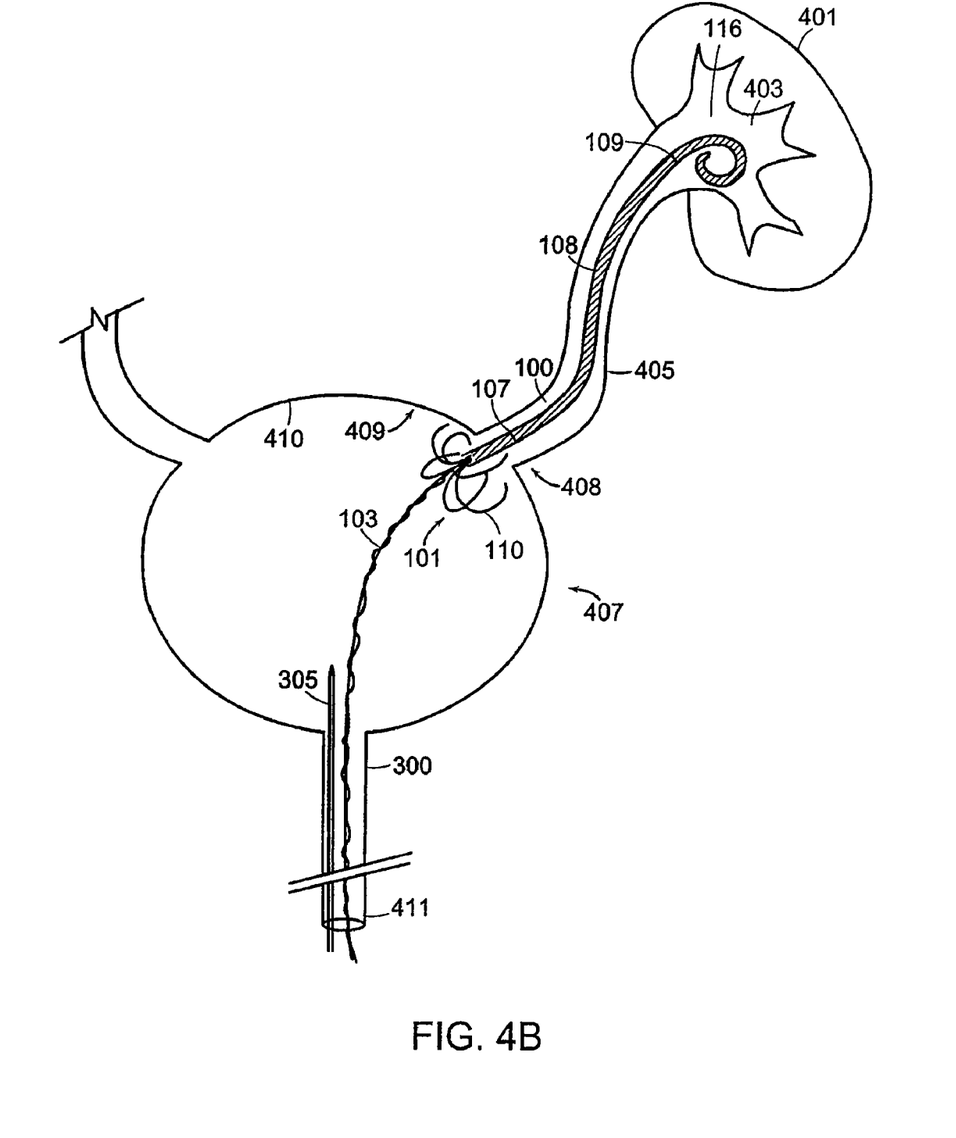

Referring to FIGS. 1, 4A, and 4B, the radially extending flexible segments 110 reduce patient discomfort by minimizing contact with the trigone region 409 of the bladder 407. At least one of the radially extending flexible segments 110 is able to assume an outwardly everted configuration, such that a portion of the at least one segment 110 is substantially perpendicular to the longitudinal axis 204 of the central body 108. In a particular embodiment, all of the radially extending flexible segments 110 are able to assume an outwardly everted configuration, allowing the proximal retention structure 101 to maintain a relatively compact shape, thus minimizing contact to the trigone region 409 of the bladder 407.

Should the proximal retention structure 101 contact a bladder wall 410 abrasion and irritation of the bladder 407 are further reduced by minimizing the force of contact of the radially extending flexible segments 110 against the sensitive regions of the bladder 407. The radially extending flexible segments 110 are generally thin, narrow and light in weight. Additionally, the segments 110 are constructed from a flexible material that readily yields to pressure exerted by the bladder wall 410. As such, when the proximal retention structure 101 contacts the bladder wall 410, much of the force of contact is absorbed by the flexible segments 110. When absorbing the force of contact the radially extending flexible segments 110 collapse on an axis substantially perpendicular to the longitudinal axis 204 of the central body 108. Accordingly, the outside diameter 150 of the proximal retention structure 101 remains greater than the diameter of the ureter, thus inhibiting migration of the stent 100 through the ureter 405.

Additionally, the force of contact of the proximal retention structure 101 against the bladder wall 410 may be further reduced due to the configuration of the radially extending flexible segments 110. In one embodiment, as shown in FIG. 1, the radially extending flexible segments 110 may be outwardly everted such that the distal ends 111 of the segments 110 are generally orthogonal to the proximal end 107 of the central body 108. In this configuration, the portion of the radially extending flexible segment 110 that contacts the bladder wall 410 is generally planar. Consequently, when the proximal retention structure 101 contacts the bladder wall 410, abrasion and irritation to the sensitive regions of the bladder 407 is minimized. Moreover, the radially extending flexible segments 110 are constructed from a resilient material, allowing the segments 110 to regain their original shape after being deformed.

In operation, the central body 108 of the stent 100 is positioned in the urinary tract of a patient between the bladder 407 and a kidney 401 and extends along the entire length of the ureter 405 (See FIGS. 4A and 4B). Alternatively, the stent 100 may be used in other bodily lumens. The proximal retention structure 101 is positioned within the bladder 407 and the distal retention structure 116 is positioned within the renal pelvis 403 of the kidney 401 (See FIG. 4B). At the proximal portion 102, the proximal retention structure 101 functions as an anchor to inhibit migration of the stent 100 through the ureteral-vesical junction 408. A retraction structure 103 can be disposed adjacent to the proximal retention structure 101 to allow the stent 100 to be removed without using a cytoscope. The retraction structure 103 can be a thread-like structure that is disposed in the urethra and extends outside of the patient when the stent 100 is in use.

The distal portion 106 of the elongated member 118 is located within the renal pelvis 403 when the stent 100 is positioned in the patient. The distal portion 106 forms a distal retention structure 116 that functions as an anchor to prevent the migration of the stent 100 out of the renal pelvis 403 and down into the ureter. To prevent the distal portion 106 from passing through the ureter 405, an overall outside dimension 154 of the distal retention structure 116 should exceed the outside diameter 170 of the distal end 109 of the central body 108. The shape of the distal retention structure 116 may be a coil 112. Alternatively, the distal retention structure 116 may assume the configuration of a pigtail, J-shape, or a helical coil, for example.

FIGS. 4A and 4B illustrate a method of inserting the stent 100 into the ureter 405 of a patient. The ureteral stent 100 in FIGS. 4A and 4B is shown disposed within the flexible sheath 300. As shown in FIG. 4A, a medical professional inserts the ureteral stent 100 and the flexible sheath 300 into the patient's bladder 407 by advancing the stylet 305 through the urethral opening 411 of the patient. The stylet 305 is further advanced up into the ureter 405, transporting the ureteral stent 100 and the flexible sheath 300 into the desired location. So that the physician can confirm the proper placement of the stent 100 by radiographic techniques, a small amount of metal or other radiopaque material, such as, for example, bismuth, may be embedded within the elongated member 118 or alternatively at the distal end 307 of the stylet 305.

Once the stent 100 is properly positioned in the patient's body, the medical professional removes the flexible sheath 300 by drawing the sheath retraction structure 303 out of the body. The drawing action causes the ureteral stent 100 to slip through an opening 310 in the flexible sheath 300 and remain positioned in the ureter. When drawing the sheath retraction structure 303 out of the body, a sufficient amount of counter-force should be applied to the stylet 305 to maintain the proper position of the ureteral stent 100. Removal of the flexible sheath 300 allows the flexible segments 110 to regain their original shape, thus inhibiting upward migration of the stent 100. After the flexible sheath 300 is removed from the patient, the stylet 305 may be retrieved from the patient's body.

To ensure that the stent 100 maintains its position within the ureter 405, the stylet 305 should be retrieved from the patient at a relatively slow pace to avoid displacing the stent 100 from its position in the ureter 405. As the stylet 305 is removed from the distal end 109, the distal retention structure 116 is able to assume a configuration that inhibits movement down the ureter 405. Thus, the stylet 305 may be retrieved at a progressively faster pace as the distal retention structure 116 regains its original shape.

Alternatively, the flexible sheath 300, once removed from the stent 100, can be used as a pusher for preventing migration of the stent 100 while withdrawing the stylet 305. More particularly, the flexible sheath 300 is removed from the stent 100, but remains in the bladder 407, adjacent to the proximal retention structure 101. As the stylet 305 is retrieved from the patient, the flexible sheath 300 is pushed upward against the proximal retention structure 101, thus preventing the stent 100 from migrating down the ureter 405. Indeed, when removing the stylet 305 from the stent 100, a sufficient amount of counter-force should be applied to the proximal retention structure 101 to maintain the proper position of the stent 100 within the ureter 405. Once the stylet 305 is removed from the stent 100, both the stylet 305 and the flexible sheath 300 can be retrieved from the body of the patient.

FIG. 4B shows the distal retention structure 116 positioned within the renal pelvis 403 of the kidney 401 and the radially extending flexible segments 110 positioned in the bladder 407. After the stent 100 is properly placed, a medical professional retracts the stylet 305 through the urethral opening 411 leaving the stent 100 in the ureter 405 of the patient. Once the stylet 305 is removed from the stent 100, the distal retention structure 116 is deployed, thereby inhibiting migration of the stent 100 out of the kidney 401.

Once inserted into the body, the stent 100 operates to drain urine from the kidney 401 to the bladder 407. Referring to FIGS. 1 and 4B, drainage of urine occurs by receiving at least some of the urine into the lumen 105 through at least one opening 114 disposed in the distal portion 106. Thereafter, the urine passes through the lumen 105 within the central body 108 and the proximal portion 102 until reaching the opening 104 where the urine empties into the bladder 407. The urine may then be expelled from the body under the natural control of the patient.

While the stent 100 is in use, the retraction structure 103 remains attached to the stent 100 and extends outside the patient through the urethral opening 411. The length of the retraction structure 103 in the proximal portion 102 may vary depending on the size of the patient. When use of the ureteral stent 100 is no longer required, a medical professional removes the stent 100 by drawing the retraction structure 103 out of the patient, which causes the stent 100 to migrate down the ureter 405 and out of the patient though the urethral opening 411.

During retraction, the retention structures 101 and 116 assume substantially linear configurations in response to the force exerted by the medical professional. Particular, the distal portion 106 is linearized as the renal pelvis 403 exerts force on the distal retention structure 116 while exiting the kidney 401. Similarly, the proximal portion 102 assumes a substantially linear configuration as the segments 110 are folded over the proximal end 107 of the central body 108. In this configuration, the distal ends 111 of the radially extending segments 110 are generally parallel to the longitudinal axis 204 of the central body 108. Once removed from the body, the stent 100 regains its original shape.

Figure 5A:
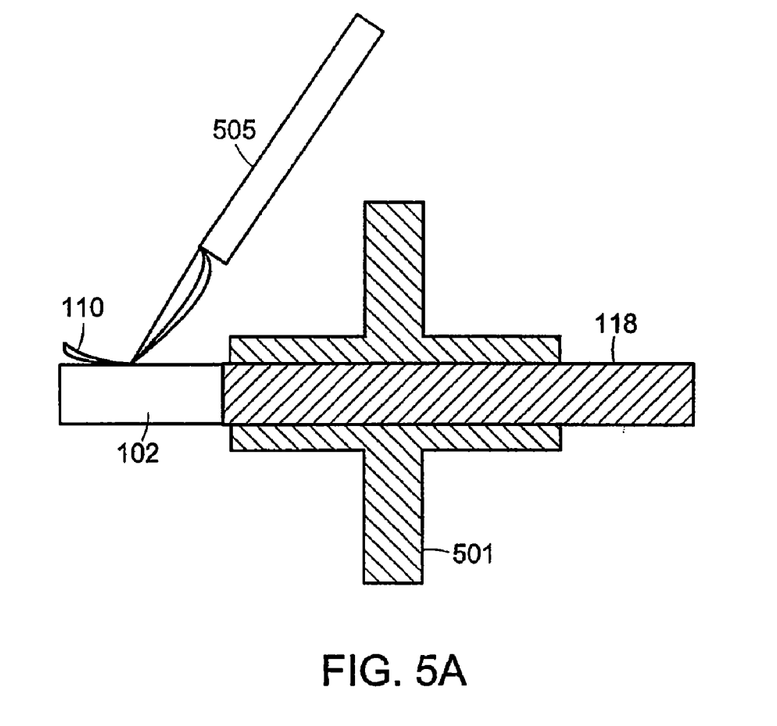
FIGS. 5A-5D are schematic representations of various methods of making the stent of FIG. 1.

Various methods may be used to produce the stent 100. FIGS. 5A-5D illustrate various methods of making the radially extending flexible segments 110. As shown in FIG. 5A, the radially extending flexible segments 110 may be formed by securing the elongated member 118 in an indexing fixture 501 and longitudinally sectioning the proximal portion 102 into segments 110 (one shown) using a cutting tool 505.

In one embodiment, the segments 110 have widths 156 that are substantially uniform. In that embodiment, the slices 130 (See FIG. 5B) formed by the cutting tool 505 are equally spaced around the proximal portion 102 of the stent 100 to produce a particular number of segments 110. The width 156 of an individual segment 110 is dependent on a diameter 158 of the proximal portion 102 and the number of segments 110 produced from the proximal portion 102. For example, a proximal portion 102 with a 9 French diameter may produce six segments 110, where each segment 110 has a width 156 of about 1.5 mm. The number and width 156 of the segments 110 can vary to suit a particular application.

Figure 5B:
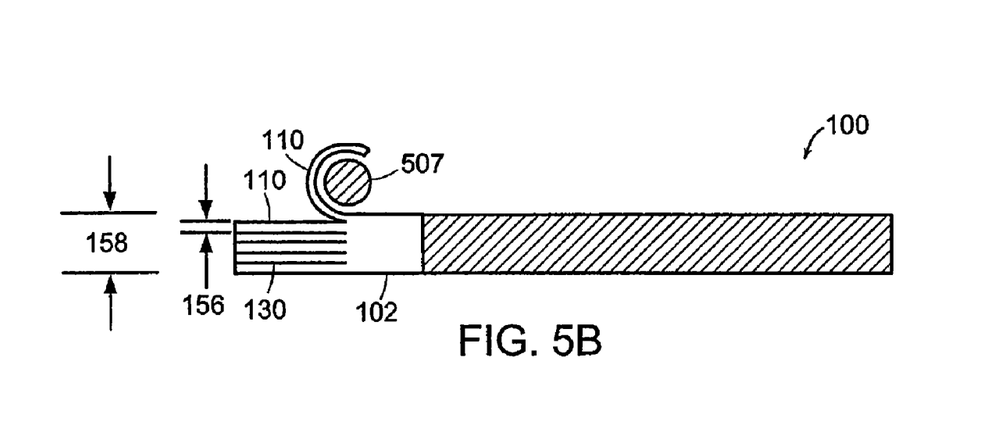

After the proximal portion 102 is sectioned, the segments 110 can be form molded and fixed into an outwardly everted configuration, as illustrated in FIG. 5B. In one embodiment, the segments 110 at the proximal portion 102 can be conformed to a mold 507 and fixed by methods commonly known in the art. For example, fixation can occur by thermosetting the formed segments 110 at about 140 to about 170° C.

The ureteral stent 100 may be constructed of a biocompatible plastic, such as but not limited to, polyester, nylon based biocompatible polymers, polytetrafluoroethylene polymers, silicone polymers, polyurethane polymers polyethylene polymers, and thermoplastic polymers. In a particular embodiment, the stent 100 is constructed of ethylene vinyl acetate. The elongated member 118 may be formed by extrusion or injection molding techniques commonly known in the art.

Figure 5C:
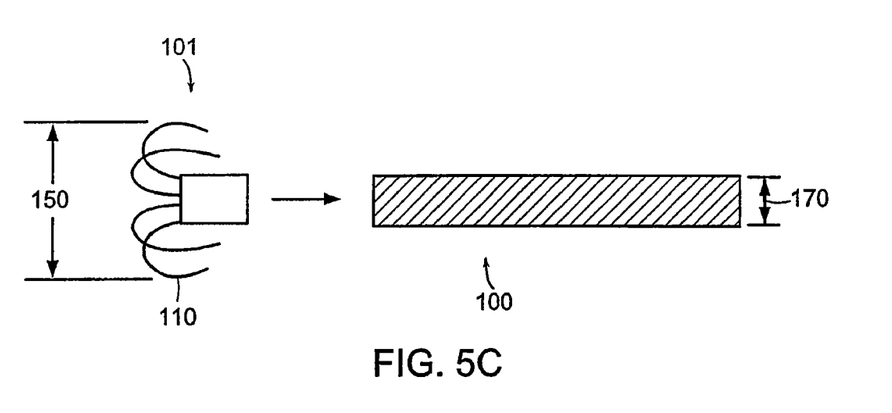
Figure 5D:
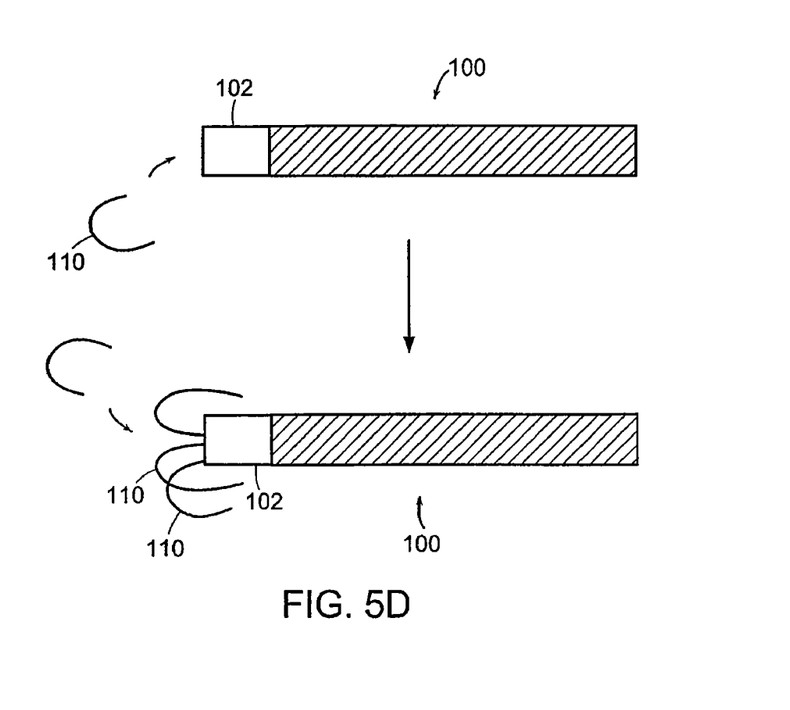

FIG. 5C shows an alternative embodiment of the invention where the proximal retention structure 101 is manufactured separately to include the radially extending flexible segments 110 and later attached to the stent 100. FIG. 5D illustrates another alternative embodiment where each radially extending flexible segment 110 is individually manufactured and separately attached to the proximal portion 102 of stent 100. Attachment of the components may be carried out using biocompatible adhesives or various bonding techniques, such as ultrasonic and radio frequency bonding.

Bonding of the components may be performed by heat bonding. Heat bonding functions by partially melting the plastic of a structure, allowing the melted plastic to adhere to a contacting surface or other component, and allowing the plastic to cool and harden, thus forming a bond. Heat bonding methods that include radio frequency bonding, induction heating, and conduction heating may be used. The plastic of a first component may be selected to melt at a similar temperature as a second component so that both components are melted during the heat bonding process. Alternatively, either the first or second component may be constructed from a plastic with a lower melting temperature than the other component in order that only the component with the lower melting temperature may melt during the bonding process.

Alternatively, the components may be bonded by the use of a solvent, such as cyclohexanone and methylethylketone. The solvent acts by dissolving and swelling the plastic of the components. As the plastic of the components dissolve and swell, the components adhere to each other. The solvent is then removed allowing for the dissolved and swollen plastic to harden and thus complete the bonding process.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of embodiments of the invention is not intended to be limiting.

The invention claimed is:

1. A stent, comprising:
an elongated member defining a lumen extending at least partially therethrough and having a length sufficient to extend substantially along an entire length of a ureter of a patient, the elongated member including a proximal end and a distal end;
a plurality of flexible segments each including a first end and a second end, the first end of at least one flexible segment of the plurality of flexible segments disposed adjacent the proximal end of the elongated member, the at least one of the plurality of flexible segments being biased towards a first position in which the at least one flexible segment extends from the proximal end of the elongated member such that the second end of the at least one flexible segment is disposed distal of the first end of the at least one flexible segment and proximal of the distal end of the elongated member and in which at least a portion of the at least one flexible segment is orthogonal to a longitudinal axis of the elongated member,
the plurality of flexible segments are configured to move between the first position and a second position, the at least one flexible segment being substantially parallel to the longitudinal axis of the elongated member such that the first end of the at least one flexible segment is disposed distal of the second end of the at least one flexible segment and proximal of the distal end of the elongated member when the plurality of flexible segments are in the second position, the plurality of flexible segments defining an outer diameter that is not greater than an outer diameter of the elongate member when the plurality of flexible segments are in the second position; and
a retention structure disposed adjacent the distal end of the elongated member, the retention structure having a coiled shape configured to retain a portion of the stent within a kidney when the stent is placed within the patient.

2. The stent of claim 1, wherein:
when the plurality of flexible segments are in the second position, the plurality of flexible segments define a lumen having a longitudinal axis that is substantially coaxial with thea longitudinal axis of the elongated member.

3. The stent of claim 1, wherein the plurality of flexible segments have a size along an axis substantially orthogonal to the longitudinal axis of the elongated member when the plurality of flexible segments are in the first position, the size being larger than an outside diameter of the elongated member at the proximal end of the elongated member.

4. The stent of claim 1, wherein each flexible segment of the plurality of flexible segments is resilient.

5. The stent of claim 1, wherein:
when the plurality of flexible segments are in the second position, at least a portion of each flexible segment is in contact with an adjacent flexible segment such that the plurality of flexible segments define a lumen having a longitudinal axis that is substantially coaxial with the longitudinal axis of the elongated member.

6. The stent of claim 1, wherein an outside dimension of the retention structure is larger than an outside diameter of the elongated member at the distal end.

7. The stent of claim 1, wherein the plurality of flexible segments are integrally formed with the elongated member.

8. A stent, comprising:
an elongated member including a proximal end, a distal end and a central portion disposed therebetween, the central portion defining a lumen extending at least partially therethrough and having a length sufficient to extend substantially along an entire length of a ureter of a patient;
a distal retention structure disposed adjacent to the distal end, the distal retention structure having a coiled shape and being configured to retain a portion of the stent within a kidney after placement of the stent within the patient; and
a proximal retention structure disposed adjacent to the proximal end of the elongated member, the proximal retention structure having a plurality of flexible segments, each flexible segment from the plurality of flexible segments having a first end disposed adjacent the proximal end of the elongated member and a second end, the proximal retention structure having a first configuration and a second configuration,
when the proximal retention structure is in the first configuration, a portion of each flexible segment from the plurality of flexible segments abuts a portion of an adjacent flexible segment such that the plurality of flexible segments collectively has a substantially circular cross-section in a plane substantially orthogonal to a longitudinal axis of the elongated member,
when the proximal retention structure is the first configuration, the first end of each flexible segment is disposed distal of the second end of each flexible segment and proximal of the distal end of the elongated member,
when the proximal retention structure is in the second configuration, the second end of at least one flexible segment from the plurality of flexible segments is spaced apart from the second end of its adjacent flexible segment from the plurality of flexible segments such that the second end of the at least one flexible segment is disposed distal of the first end of the at least one flexible segment and proximal of the distal end of the elongated member,
when the proximal retention structure is in the second configuration, at least a portion of the at least one flexible segment is orthogonal to the longitudinal axis of the elongated member.

9. The stent of claim 8, wherein the proximal end of the elongated member and the proximal retention structure are monolithically formed.

10. The stent of claim 8, wherein the proximal retention structure is biased towards the second configuration.

11. The stent of claim 8, wherein the proximal retention structure is configured to be moved between the first configuration and the second configuration when disposed within a bladder of the patient.

12. The stent of claim 8, wherein the proximal retention structure has a size along an axis substantially orthogonal to the longitudinal axis of the elongated member when the proximal retention structure is in the second configuration, the size being larger than an outside diameter of the proximal end of the elongated member.

13. The stent of claim 8, wherein the proximal retention structure defines a lumen when the proximal retention structure is in the first configuration, a diameter of the lumen of the proximal retention structure being substantially equal to a diameter of the lumen defined by the elongated member.

14. The stent of claim 8, wherein each of the plurality of flexible segments has a substantially arcuate cross-section.

* * * * *